(12) United States Patent
Stroefer et al.

(10) Patent No.: US 7,179,935 B2
(45) Date of Patent: Feb. 20, 2007

(54) METHOD FOR PRODUCING ISOCYANATES

(75) Inventors: Eckhard Stroefer, Mannheim (DE);
Michael Ochse, Bad Duerkheim (DE);
Volker Krase, Lauchhammer (DE);
Andreas Schmidt, Schwarzheide (DE);
Matthias Kloetzer, Kroppen (DE);
Imbridt Murrar, Senftenberg (DE);
Gisbert Franzke, Schwarzheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 118 days.

(21) Appl. No.: 10/504,320

(22) PCT Filed: Feb. 28, 2003

(86) PCT No.: PCT/EP03/02131

§ 371 (c)(1),
(2), (4) Date: Aug. 24, 2004

(87) PCT Pub. No.: WO03/074477

PCT Pub. Date: Sep. 12, 2003

(65) Prior Publication Data

US 2005/0154227 A1   Jul. 14, 2005

(30) Foreign Application Priority Data

Mar. 1, 2002  (DE) ............................ 102 09 095

(51) Int. Cl.
*C07C 263/00* (2006.01)
(52) U.S. Cl. .......................... 560/345; 560/336
(58) Field of Classification Search ............... 560/330, 560/336, 345, 338
See application file for complete search history.

(56) References Cited

U.S. PATENT DOCUMENTS

| 3,734,941 A | 5/1973 | Sydor |
| 5,616,784 A * | 4/1997 | Schwarz et al. ............ 560/345 |

FOREIGN PATENT DOCUMENTS

| DE | 2 421 503 | 11/1974 |
| EP | 0 092 738 | 11/1983 |
| EP | 396976 | * 11/1990 |
| EP | 0 524 554 | 1/1993 |
| EP | 0 568 782 | 11/1993 |

* cited by examiner

*Primary Examiner*—Thurman K. Page
*Assistant Examiner*—Karl Puttlitz
(74) *Attorney, Agent, or Firm*—Oblon, Spivak, McClelland, Maier & Neustadt, P.C.

(57) ABSTRACT

A process for the preparation of isocyanates from carbamic esters.

8 Claims, 4 Drawing Sheets

METHOD FOR PRODUCING ISOCYANATES

The present invention relates to a process for the preparation of isocyanates by thermal cleavage of carbamic esters.

It is known that isocyanates can be prepared by a process which manages without the use of phosgene. In said process, an amine is reacted with an alcohol and urea to give the corresponding carbamic ester (urethane). The carbamic ester is then subjected to thermal cleavage to give the isocyanate, the alcohol being liberated again.

The cleavage of the carbamic esters can take place in the gas phase or in the liquid phase. The cleavage of the carbamic esters after vaporization in the gas phase, described, for example, in U.S. Pat. No. 3,734,941, has the disadvantage of the danger of blockage in the upstream evaporator. The cleavage in the liquid phase makes it necessary to remove one of the two products of the cleavage reaction from the reaction mixture in order to prevent a back-reaction. Usually, both cleavage products are removed in gaseous form and then separated.

For the preparation of polyfunctional isocyanates, in which there is a greater danger of polymerization and residue formation, DE-A 24 21 503 proposes the dilution of the carbamic esters with inert solvents. The presence of inert solvents means a greater expense. EP-A 92 738 proposes solvent-free cleavage. Thin-film evaporators and falling-film evaporators are mentioned as suitable cleavage reactors.

EP-A 0 524 554 discloses a process for the solvent-free cleavage of carbamic esters. In said process, hexamethylenedi-n-butylurethane is cleaved continuously in a heating plug reactor at 240° C. and 30 mbar. The cleavage gases are separated in a rectification column which is present on the reactor and has a reflux and a side take-off.

The intermediate cooling described in EP 0 568 782, with heat recovery in the lower third of a combined cleavage and rectification column by means of a tube-bundle heat exchanger, has the disadvantage of caking and/or blockage of the apparatus. This disadvantage is exacerbated by the addition of the urethane to be cleaved above the heat exchanger.

It is an object of the present invention to provide an improved process for the solvent-free cleavage of carbamic esters.

We have found that this object is achieved by a process for the preparation of isocyanates from carbamic esters, in which (i) a mixture containing a monofunctional or polyfunctional carbamic ester is passed continuously into a cleavage reactor or a cascade of two or more cleavage reactors, (ii) the carbamic ester is subjected to a thermal cleavage to give isocyanate and alcohol, (iii) the cleavage gas escaping from the cleavage reactor or reactors and containing the isocyanate, the alcohol, possibly uncleaved and/or partly cleaved carbamic ester and byproducts is brought at least partially into contact with a liquid coolant and condensing agent, cooled and at least partly condensed and (iv) the isocyanate and the alcohol are obtained from the cooled cleavage gas and the condensate in a rectification column, a part-stream of the alcohol obtained being used as liquid coolant and condensing agent for cooling and condensing the cleavage gas.

It has surprisingly been found that the isocyanate yield of the carbamic ester cleavage and subsequent separation of the cleavage products in a rectification column can be considerably improved if the cleavage gases are cooled and at least partly condensed using a liquid coolant and condensing agent before carrying out the rectification. The coolant and condensing agent is expediently the alcohol liberated in the cleavage reaction and recovered in the rectification column.

In addition to the isocyanate and the alcohol, the cleavage gases usually also contain uncleaved and—in the cleavage of polyfunctional carbamic esters—also partly cleaved carbamic esters, for example the monourethane in the case of the cleavage of diurethanes.

Furthermore, the cleavage gases may contain byproducts, such as carbonates, carbamates and carbon dioxide.

Carbamic esters which are cleaved by the novel process are monofunctional or polyfunctional carbamic esters, preferably bifunctional carbamic esters. Examples of isocyanates which are prepared by the novel process are 1,4-diisocyanatobutane, 1,6-diisocyanatohexane (HDI), 2-methyl-1,5-diisocyanatopentane, 1,5-diisocyanato-2,2-dimethylpentane, 2,4,4-trimethyl-1,6-diisocyanatohexane, 1,10-diisocyanatodecane, 1,3- and 1,4-diisocyanatocyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane, 1-isocyanato-1-methyl-4(3)-isocyanatomethylcyclohexane (IMCI), bis(isocyanatomethyl)norbornane, 2,4- and 2,6-diisocyanatotoluene (TDI), 2,4'- and 4,4'-diisocyanatodiphenylmethane and higher homologs, 1,5-diisocyanatonaphthalene, dipropylene glycol diisocyanate, triisocyanates and/or isocyanates having a higher functionality, e.g. 4-isocyanatomethyloctane 1,8-diisocyanate (nonane triisocyanate), 1,6,11-undecane triisocyanate or any desired mixtures of such isocyanate compounds. Examples of alcohols which are contained in the carbamic esters to be cleaved according to the invention and act as coolants and condensing agents are methanol, ethanol, n-propanol and n-butanol. A particularly preferred carbamic ester is hexamethylenedi-n-butylurethane (HDU).

The cooling and condensation step (iii) can be carried out in a separator which is present upstream of the rectification column. There, the liquid alcohol is fed as a coolant and condensing agent by means of a suitable distributor, for example a spray nozzle, into the hot gas stream which leaves the cleavage reactor. The gases thus cooled can be further cooled by means of a heat exchanger, for example a tube-bundle heat exchanger.

The condensation step (iii) is preferably carried out in the rectification column itself. For this purpose, the cleavage gas is fed into the rectification column at the bottom of the column and the part-stream of the alcohol obtained, which acts as coolant and condensing agent, is fed into the rectification column in the lower column section, preferably at the height of the 1st to 4th theoretical plate, in particular at the height of the 1st theoretical plate, and is passed countercurrent to the ascending cleavage gas.

Suitable rectification columns are conventional tray columns or columns containing stacked or dumped packings and usually have from 8 to 25 theoretical plates.

The rectification column has a reflux at the top of the column, a side take-off for removing the higher-boiling cleavage product (isocyanate or alcohol) and a top take-off for removing the lower-boiling cleavage product. Usually, the alcohol is the lower-boiling cleavage product and is obtained as a top take-off stream at the top of the column. The isocyanate is accordingly obtained as a side take-off stream. However, the opposite case is also possible.

The reflux ratio is usually from 1 to 4. Usually, a part-stream of from 5 to 40% of the alcohol removed as a top take-off stream or side take-off stream, preferably as a top take-off stream, is removed as a coolant and condensing agent and fed into the lower part of the columns.

At the bottom of the column, uncleaved and any partly cleaved carbamic esters are usually obtained. These are preferably recycled into the cleavage reactor.

Suitable cleavage reactors are those which contain internals for the introduction of the heat of reaction. Examples are Robert evaporators, Herbert evaporators, heating plug evaporators, Caddle-type evaporators, tube-bundle reactors, kettles having an internal heating coil and similar reactors which permit introduction of a large amount of heat into a small volume. The reaction medium is present therein in a boiling-like state in which the gases and vapors of the starting material which result from the cleavage reaction are formed and ascend in the liquid. The reactors are preferably operated, as described in EP-A 0 524 554, in such a way that the two-phase mixture comprising boiling liquid and vapor phase of the vaporized starting material and the cleavage gases has a volumetric gas content of more than 50%. The residence time of the boiling liquid in the reactor is from 1 to 60, preferably from 5 to 30, minutes. The reaction is carried out without any addition of solvent or diluent.

The examples which follow illustrate the invention.

EXAMPLES

Comparative Example 1

Figure 1:
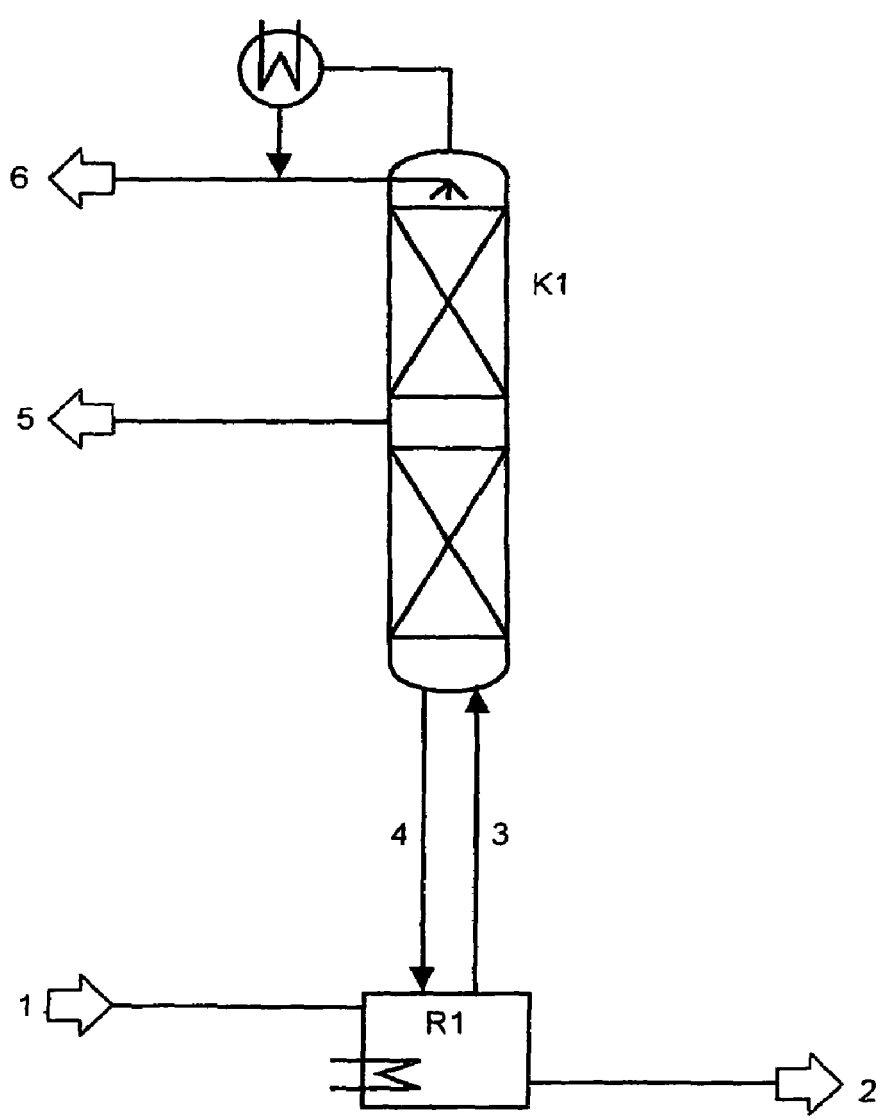
FIG. 1 shows an apparatus for carrying out a comparative process which includes a cleavage reactor R1 and a rectification column K1.

The cleavage reaction and the working-up of the cleavage gases are carried out in the apparatus shown in FIG. 1. In the cleavage reactor R1, 4 kg/h of a mixture of 80% by weight of 2,4-toluenedi-n-butylurethane and 20% by weight of 2,6-toluenedi-n-butylurethane are fed in as stream 1. The reactor temperature is about 240° C., the reactor pressure about 100 mbar and the average residence time of the reaction mixture in the cleavage reactor about 10 minutes. The thermal power introduced is about 3.4 kW. The cleavage gases are separated in the rectification column K1, which has 10 theoretical plates. The cleavage gas stream 3 is fed into the bottom of the column. At the height of the 5th theoretical plate, a side take-off stream 5 of 1.3 kg/h of tolylene diisocyanate (TDI) having a purity of 93% by weight is taken off. 1.6 kg/h of n-butanol having a purity of 98% by weight are taken off as top take-off stream 6. The temperature in the top condenser is about 36° C. and the pressure is about 20 mbar. The bottom take-off stream 4 of about 14 kg/h contains about 70% by weight of TDI and 20% by weight of semicleaved urethane and is passed back into the reactor R1. The reactor discharge stream 2 of about 1.1 kg/h contains about 80% by weight of low molecular weight and high molecular weight allophanates.

The yield of tolylene diisocyanate is about 60.8%, based on toluenedi-n-butylurethane used.

Example 1

Figure 2:
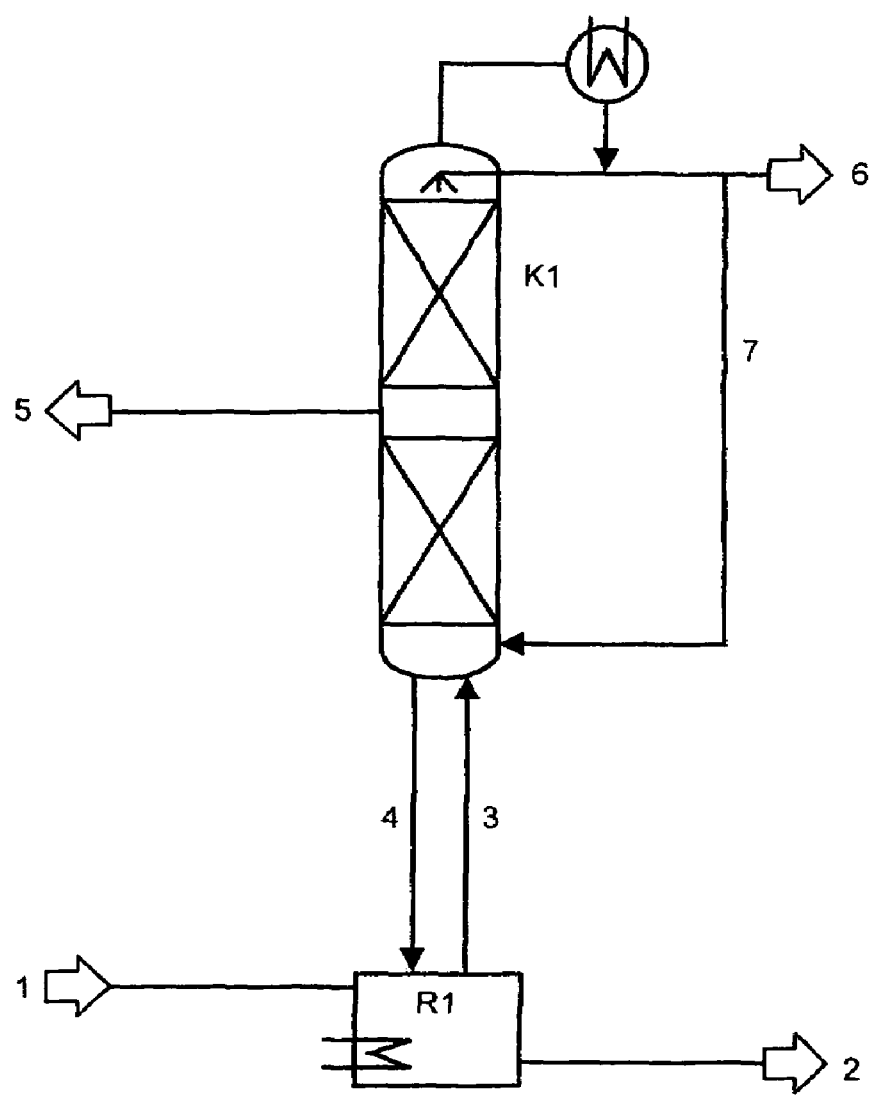
FIG. 2 shows an apparatus for carrying out one embodiment of the invention which includes a cleavage reactor R1 and a rectification column K1.

The cleavage reaction and working-up of the cleavage products are carried out in the apparatus shown in FIG. 2. This is the same as the apparatus according to FIG. 1 (comparative example), except that a stream 7 of 0.8 kg/h of liquid n-butanol, which is removed from the top take-off stream, is fed in as coolant and condensing agent at the height of the 1st theoretical plate. Under otherwise identical operating conditions (reactor feed 1=4 kg/h, reactor temperature=240° C., power introduced 3.9 kW, top take-off stream 6=1.6 kg/h, column pressure 20 mbar), the side take-off stream 5 could be increased from 1.3 kg to 1.5 kg. The reactor discharge stream 2 thus decreased from about 1.1 kg/h to about 0.9 kg/h.

The yield of tolylene diisocyanate consequently improved from 60.8 to 66.2%.

Comparative Example 2

The cleavage reaction and the working-up of the cleavage gases are carried out in the apparatus shown in FIG. 1. In the cleavage reactor R1, 4 kg/h of a mixture of 89% by weight of hexamethylenedi-n-butylurethane are fed in as stream 1. The reactor temperature is 238° C., the reactor pressure about 35 mbar and the average residence time of the reaction mixture in the cleavage reactor about 25 minutes. The thermal power introduced is about 1.4 kW. The cleavage gases are separated in the rectification column K1, which has 25 theoretical plates. The cleavage gas stream 3 is fed into the bottom of the column. At the height of the 14th theoretical plate, a side take-off stream 5 of about 1.3 kg/h of hexamethylene diisocyanate having a purity of 97.5% by weight is taken off. About 1.4 kg/h of n-butanol having a purity of 97% by weight are removed as top take-off stream 6. The temperature in the top condenser is about 28° C. and the pressure about 20 mbar. The column take-off stream 4 of 3.7 kg/h contains about 60% by weight of semicleaved urethane, 15% by weight of urethane and allophanates. This stream is passed back into the cleavage reactor. The reactor discharge stream 2 of about 1.3 kg/h contains about 70–80% by weight of higher-boiling compounds, e.g. allophanates.

The yield of hexamethylene diisocyanate is about 67%, based on the urethane used.

Example 2

Figure 3:
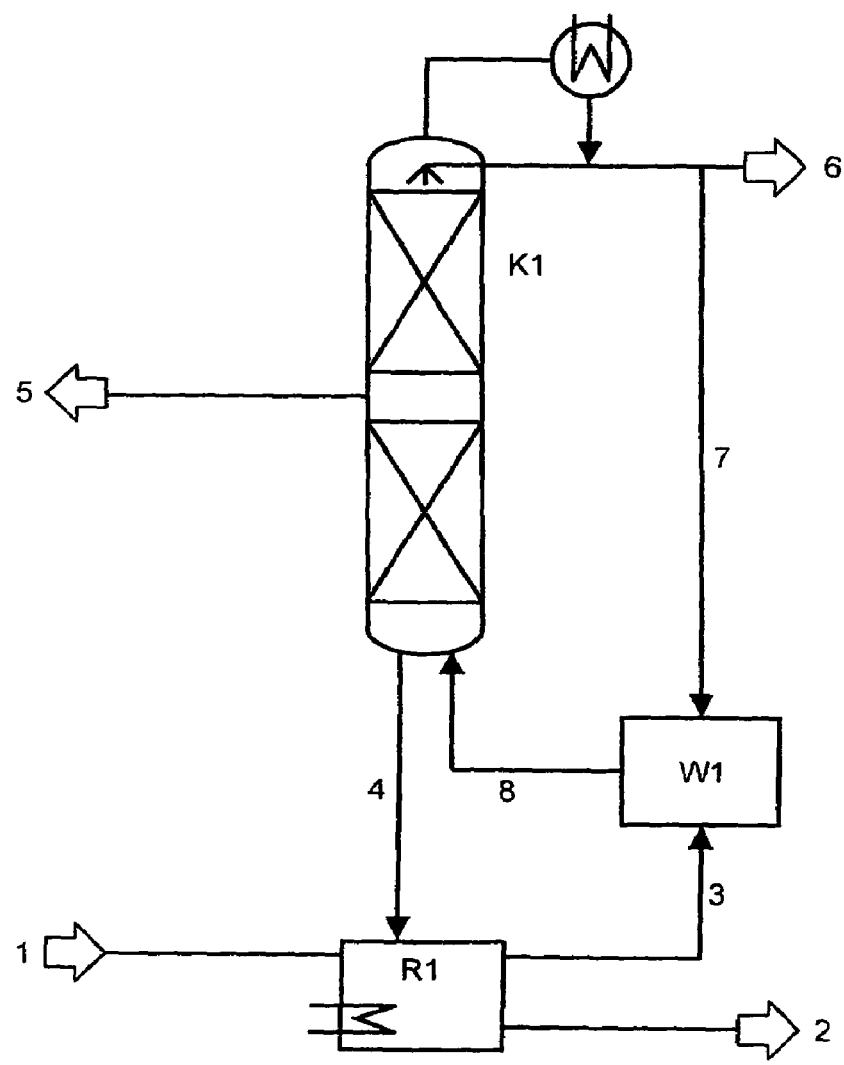
FIG. 3 shows an apparatus for carrying out one embodiment of the invention which includes a cleavage reactor R1, a rectification column K1, and a condenser W1.

The cleavage reaction and working-up of the cleavage gases are carried out in the apparatus shown in FIG. 3. This is the same as the apparatus according to FIG. 1 (comparative example 2), except that the gases which leave the cleavage reactor are cooled with n-butanol in a separate condenser W1 and fed to the rectification column. The rectification column could be reduced to 10 theoretical plates by the use of the separate condenser W1. The reaction conditions in the cleavage reactor are identical to those in comparative example 2. A reactor feed 1 of 4 kg/h of 89% by weight of hexamethylenediurethane is metered into the cleavage reactor R1. For cooling the cleavage gas stream 3 of 8.1 kg/h, containing about 20% by weight of hexamethylene diisocyanate, a stream 7 of about 0.5 kg/h of n-butanol from the stream 6 of liquid n-butanol obtained in the top of the column K1 is pumped into the separate condenser W1. In addition, a heat flow of 0.2 kW is removed at the condenser W1 by means of thermostating. The material stream 8 leaving the condenser and having a gas content of about 80% and a temperature of about 200° C. is passed into the rectification column K1. A stream 4 of about 5.2 kg/h with about 78% by weight of semicleaved urethane and a temperature of about 180° C. is taken off from the bottom of the column K1. In the side take-off, of column K1, a stream 5 of 1.4 kg/h of hexamethylene diisocyanate with a concentration of 97.5% by weight is obtained. A stream 6 of about 1.4 kg/h of liquid n-butanol having a purity of 97% by weight is obtained at the top of the column K1.

The yield of hexamethylene diisocyanate consequently improved from 67 to 72%.

Example 3

Figure 4:
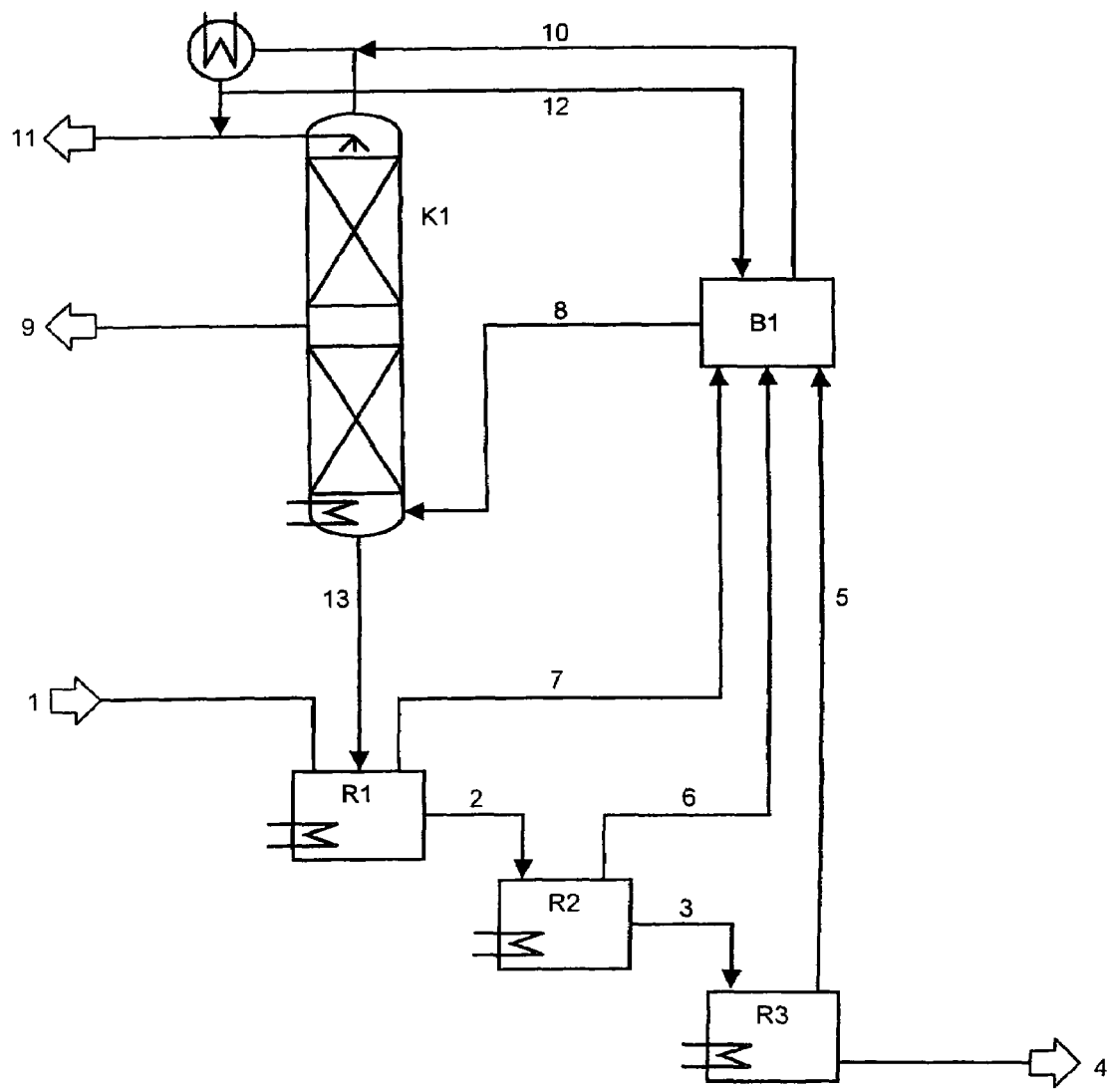
FIG. 4 shows an apparatus for carrying out one embodiment of the invention which includes a cascade of cleavage reactors R1–R3, a rectification column K2, and a condenser B1.

The cleavage reaction and working-up of the cleavage gases are carried out in the apparatus shown in FIG. 4. The cleavage reaction is effected in a cascade of reactors R1, R2 and R3. The average residence time of the reaction mixture in the reactors is from 2 to 10 minutes, the temperature from 238 to 244° C. and the pressure about 160 mbar. 4 kg/h of a feed 1 containing about 92% by weight of hexamethylenedi-n-butylurethane are fed into the first cleavage reactor R1. A liquid stream 4 of about 0.5 kg/h is removed from the last reactor R3. The cleavage gas streams 5, 6 and 7 removed from the cleavage reactors are fed into the condenser B1, comprising cooling coils and a cooling jacket. A stream 12 of 0.9 kg/h of n-butanol is fed to the condenser B1 and a condensate stream 8 of 5.5 kg/h is removed. The condensate stream 8 contains about 43% by weight of n-butanol, 36% by weight of hexamethylene diisocyanate, 2% by weight of hexamethylenedi-n-butylurethane and 16% by weight of semicleaved urethane. The condensate stream 8 is fed into the rectification column K1 at the height of the first theoretical plate. The column has 20 theoretical plates and is filled with a metal packing from MONZ. The bottom temperature in the column is about 190° C. and the top pressure about 20 mbar. At the height of the 5th theoretical plate, 1.8 kg/h of hexamethylene diisocyanate having a purity of 98%, corresponding to a yield of >90%, are removed as side take-off 9. A stream 13 of 1.2 kg/h, containing 50% by weight of hexamethylene diisocyanate and allophanates, is removed as bottom take-off and recycled to the reactor R1. At the top of the column, a stream 11 of 1.6 kg/h of n-butanol having a purity of 98% by weight is removed. The vapor stream 10 of about 0.1 kg/h which leaves the condenser B1 contains 99% by weight of n-butanol and is fed directly into the top condenser of the rectification column K1.

We claim:
1. A process for the preparation of isocyanates from carbamic esters, comprising:
   (i) continuously passing a mixture comprising a monofunctional or polyfunctional carbamic ester into a cleavage reactor or a cascade of two or more cleavage reactors,
   (ii) subjecting the carbamic ester to a thermal cleavage to obtain a cleavage gas comprising isocyanate and alcohol,
   (iii) cooling and at least partly condensing the cleavage gas, which comprises the isocyanate, the alcohol, any uncleaved and/or partly cleaved carbamic ester and byproducts, escaping from the cleavage reactor or reactors by bringing the cleavage gas into contact with a liquid coolant and a condensing agent, and
   (iv) obtaining the isocyanate and the alcohol from the cooled cleavage gas and the condensate in a rectification column,
      wherein a part-stream of the alcohol obtained is used as the liquid coolant and the condensing agent for cooling and condensing the cleavage gas.

2. The process as claimed in claim 1, wherein the rectification column comprises a bottom, and a lower column section; and wherein the cooling and condensing step (iii) is carried out in the rectification column by feeding the cleavage gas into the rectification column at the bottom of the column such that the cleavage gas ascends in the rectification column after being fed into the rectification column, feeding the part-stream of the alcohol obtained into the rectification column in the lower column section, and passing said part-stream countercurrent to the ascending cleavage gas.

3. The process as claimed in claim 1, wherein the cooling and condensing step (iii) is carried out in a separate condenser.

4. The process as claimed in claim 1, wherein the alcohol is obtained as a top take-off stream and the isocyanate is obtained as a side take-off stream.

5. The process as claimed in claim 1, further comprising a bottom-take off strearm; wherein the bottom take-off stream comprises at least one material selected from the group consisting of the uncleaved carbamic ester remaining in (iii), the partly cleaved carbamic ester remaining in (iii), and a combination thereof; and wherein the bottom take off stream is recycled into the cleavage reactor or the cleavage reactor cascade.

6. The process as claimed in claim 1, wherein the cleavage reactor or reactors are at least one reactor selected from the group consisting of a Robert evaporator, a Herbert evaporator, a Caddle-type evaporator, a tube-bundle reactor, a kettle having an internal heating coil, and a combination thereof.

7. The process as claimed in claim 1, wherein the thermal cleavage of the carbamic ester is carried out in the absence of an additional solvent.

8. The process as claimed in claim 1, wherein the carbamic ester is hexamethylenedi-n-butylurethane, the isocyanate is hexamethylene diisocyanate and the alcohol is n-butanol.

* * * * *